Figure 1:
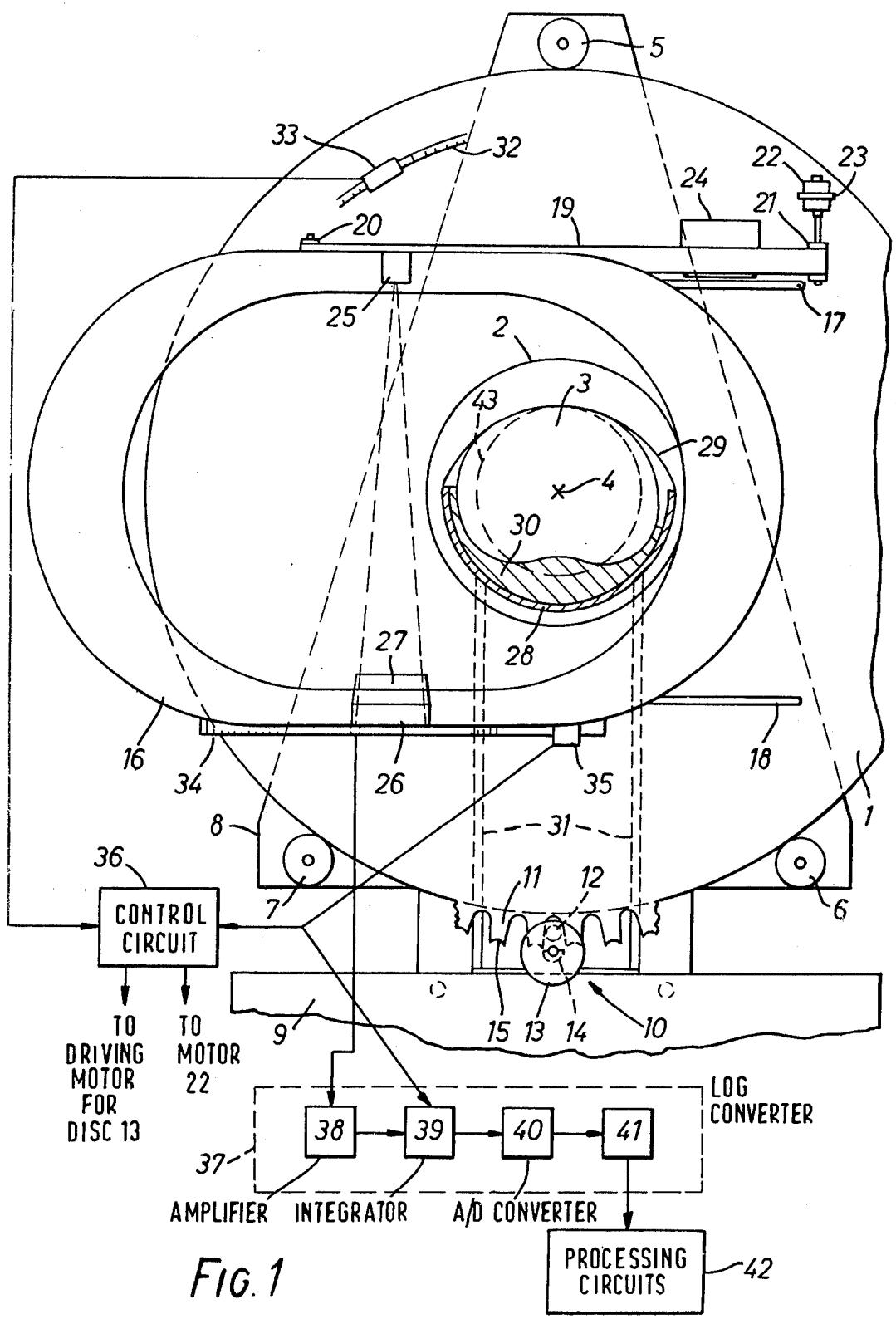

United States Patent [19]

Hounsfield

[11] 4,126,785

[45] Nov. 21, 1978

[54] RADIOGRAPHY

[75] Inventor: Godfrey N. Hounsfield, Newark, England

[73] Assignee: EMI Limited, Hayes, England

[21] Appl. No.: 796,309

[22] Filed: May 12, 1977

[30] Foreign Application Priority Data

May 18, 1976 [GB] United Kingdom ............... 20436/76

[51] Int. Cl.² ........................ A61B 6/02; G01N 23/08
[52] U.S. Cl. .................................. 250/445 T; 250/360
[58] Field of Search .................... 250/445 T, 360, 403

[56] References Cited

U.S. PATENT DOCUMENTS 3,924,131 12/1975 Hounsfield ........................... 250/360
3,952,201 4/1976 Hounsfield ....................... 250/445 T Primary Examiner—Alfred E. Smith
Assistant Examiner—T. N. Grigsby
Attorney, Agent, or Firm—Cooper, Dunham, Clark, Griffin & Moran

[57] ABSTRACT

In a computerized tomographic apparatus which involves both rotational and translational scanning movements of the source relative to the body, the translational movements are timed so that the radiation passes through, or adjacent, a mobile organ (such as the heart) of the body while that organ assumes a predetermined position, or range of positions, in its movement.

5 Claims, 2 Drawing Figures

RADIOGRAPHY

The present invention relates to radiography, and it relates especially to that branch of radiography which has become known as computerised axial tomography (CAT).

In performing CAT, radiation such as X-radiation is projected through a cross-sectional slice of a body under examination along many substantially linear beam paths, and the absorption suffered by the radiation on traversing each of the paths is measured. The measured absorption values are then processed in order to produce a representation of the absorption (or transmission) coefficients, with respect to the radiation used, at each of many elemental locations over the slice. Apparatus for performing CAT, and methods of operating the same, are described in U.S. Pat. No. 3,778,614.

The various beam paths are irradiated by scanning a source of the radiation relative to the body under examination, and detector means is provided for detecting the radiation emergent from the body along each path. The detector means usually (though not always) takes part in the scanning.

In any event, the scanning takes a finite time, and when the slice of the body contains, or lies adjacent, a mobile organ, such as the heart, which can execute significant movements during the scanning time, the representation of absorption coefficients can be degraded by artefacts caused by such movements.

It has been proposed, in U.S. Pat. No. 3,952,201, to so synchronise the irradiation of the body by the source, and the scanning, to the heartbeat of a patient that, on the one hand, the radiation is projected through the heart only when the heart assumes a particular position or range of positions and, on the other hand, the scanning is carried out at a rate which ensures expeditious examination of the body despite gaps, in the irradiation sequence of the body, which can occur when the heart assumes positions other than said particular position or range of positions. Other techniques for reducing or avoiding the production of the aforementioned artefacts are also described in said U.S. Pat. No. 3,952,201, but these other techniques are not especially relevant to the present invention, which is concerned with synchronising the scanning to the patient's heartbeat in a particularly advantageous manner.

According to the invention there is provided radiographic apparatus comprising a source of penetrating radiation disposed to project radiation through a cross-sectional slice of a patient's body along at least one substantially linear beam path, detector means disposed to receive the radiation emergent from the body along said at least one beam path, and to provide output data indicative of the amount of radiation so detected, lateral scanning means for scanning said source and detector means laterally across said slice, alternate lateral scanning movements being in opposing directions, and rotational scanning means for scanning said source and said detector means angularly around said slice, means for detecting the heartbeats of said patient and means for synchronising said lateral scanning to said heartbeats.

Figure 2:
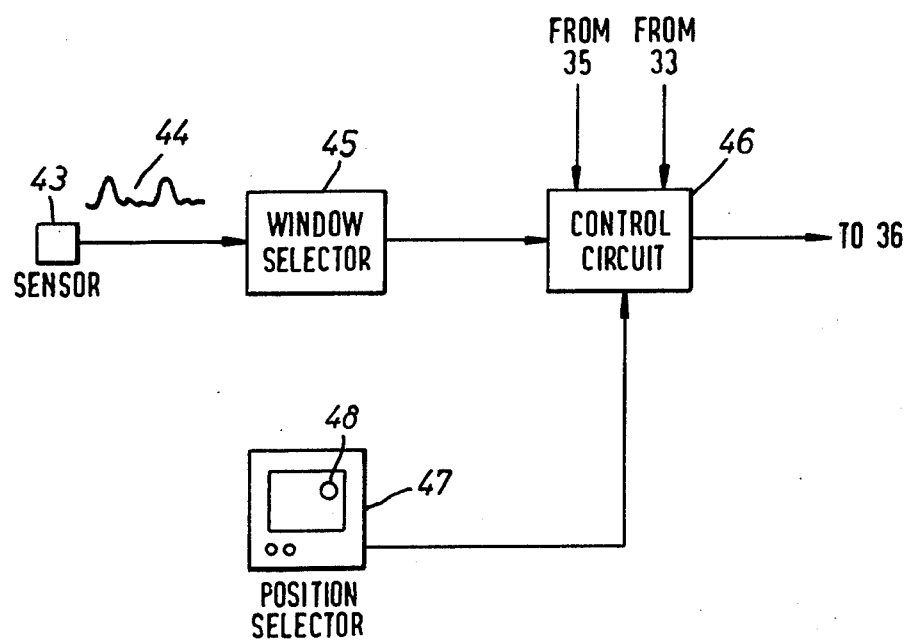

In order that the invention may be clearly understood and readily carried into effect, some embodiments thereof will now be described, by way of example only, with reference to the accompanying drawings, of which:

FIG. 1 shows, in front elevational view, one example of a radiographic apparatus suitable for use in conjunction with the present invention, and FIG. 2 shows, in block diagrammatic form, apparatus for use in one embodiment of the invention.

Referring to FIG. 1, there is shown a CAT apparatus which is generally similar to that described and claimed in U.S. Pat. No. 3,946,234. A turntable member 1 having a central aperture 2, to accommodate a body 3 to be examined, is mounted vertically for rotation about an axis 4 which is disposed centrally of the aperture 2. The member 1 is supported on three rotatable bearings 5, 6 and 7 which are journalled in a main frame 8 for the apparatus. The frame 8 remains stationary, being rigidly secured to a pedestal 9, and can take any suitable form, although it must of course be formed with an aperture coincident with the aperture 2.

The member 1 can be rotated in angular steps of (in this example) 10° by means of a Geneva mechanism generally shown at 10. The periphery of member 1 is formed with suitable prongs such as 11 which co-operate with a peg 12 on a continuously rotated disc 13 to effect the required step-wise rotary movement. The disc 13 also carries a locking cam 14 which co-operates with suitably shaped recesses such as 15 on the prongs such as 11 to effectively lock the member 1 in its angular position so long as the peg 12 is not in one of the slots formed between adjacent prongs 11. Disc 13 is journalled in the main frame 8 and is driven by an electric motor which is not shown and which is preferably capable of variable spreads of operation.

Mounted upon the turntable 1, and capable of performing a reciprocating lateral scanning motion relative thereto, is a lightweight but rigid scanning yoke 16. Yoke 16 can move on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets (not shown) secured to the member 1, and to which belt the yoke 16 is attached by means of a bracket (not shown). The roller 20 is merely an idler roller, but roller 21 is driven via a clutch device (not shown) by a reciprocating motor 22 which is attached by a strap-like bracket 23 to the member 1.

It will be appreciated that the pedestal 9 will be supported on a suitable girder or the like which ensures ground clearance of the yoke 16 in all angular positions of the turntable 1 and all lateral positions of the yoke 16 thereon.

A counter-balance weight 24 is secured to the opposite run of belt 19 to the yoke 16 and thus moves in opposition thereto to compensate for out-of-balance forces which would otherwise be set up by the lateral scanning motion of the yoke 16 and its attachments, which will now be described.

Attached to the yoke 16 is a source 25 of penetrating radiation, in this example X-radiation. The radiation is collimated to form a planar, fan-shaped beam, emanating from an effective point source. On the opposite side of yoke 16, with respect to the aperture 2, to the source 25 is an array 26 of 30 detectors sensitive to the radiation generated by the source 25, each viewing the source through a respective collimator; the collimators being disposed in a bank 27. In this example, neighbouring collimators are inclined to each other at an angle of $\frac{1}{3}°$ and since there are 30 detectors, this means that the angular spread of the beam of X-rays generated by the source 25 is 10°. The beam is not symmetrical about the perpendicular line drawn from the effective point source of the beam of X-radiation to the array 26. This line is arranged to intersect the sixteenth detector in the array 26 (counting from the left).

The body 3 is supported on a bed 28 and is secured thereon by means of straps each as 29. Gaps between the body and the bed are filled with a suitable packing material 30 which is preferably of dough-like consistency and absorbs the X-radiation to substantially the same extent as does human tissue. The material 30 is preferably contained in one or more plastic bags. The bed 28 is supported by legs 31 which stand on the pedestal 9.

It will be evident that the stepped, rotational scanning motion imparted by the Geneva mechanism 10 to the number 1 needs to be synchronised with the lateral scanning motion imparted to the yoke 16 by the reciprocating motor 22 and, to this end, the member 1 is formed with an annular graticule, part of which is shown at 32, and a fixed photodetector 33 is provided, together with a suitable light source (not shown) to provide timing pulses indicative of the passage of markings on the graticule 32 past the photodetector 33. Thus the rotational scanning motion of member 1 can be monitored, and similarly a linear graticule 34 is fixedly attached to the yoke 16 and cooperates with a second photodetector 35, which is mounted on the member 1 so as to rotate therewith, and a similarly mounted light source (not shown) to produce timing pulses indicative of the progress of the lateral scanning. Both graticules 32 and 34 comprise translucent or transparent members bearing opaque lines printed, etched or otherwise provided thereon. The two sets of timing pulses are applied to a control circuit 36 which controls the operations of the two drive motors and the clutch in the traversing drive mechanism.

Each detector in the array 26 comprises, for example, a scintillator crystal (e.g. caesium iodide) and an associated photomultiplier tube, or a photodiode, and thus provides electrical signals indicative of the amount of radiation detected thereby. The electrical signals so provided are applied to respective preprocessing circuits 37, each of which contains an amplifier 38, a resettable integrator 39, an analogue-to-digital converter circuit 40, and a logarithmic converter circuit 41. The integrators 39 are read and reset synchronously and periodically by means of timing pulses derived from the photodetector 35; the arrangement being such that the reading and re-setting occurs some 160 times during each lateral scan. Thus, during a single lateral scan, output signals are provided which are indicative of the absorption suffered by the X-radiation on traversing a set of 160 parallel paths from the source to the detector at each of 30 angular orientations with respect to the body 3. The member 1 is then rotated through 10° and another lateral scan is carried out during which a second group of 30 sets of 160 output signals are derived. The process is repeated until the member 1 has been rotated through at least 170° and all of the output signals obtained are processed in a processing circuit 42 to evaluate the absorption coefficient, with respect to the radiation used, at a plurality of locations distributed over the slice of the body 3 which lies in the plane of the beam X-rays generated by the source 25.

Preferably the processing is carried out in accordance with the technique described and claimed in U.S. Pat. No. 3,924,129 which involves a form of convolution, and preferably the output signals are applied to the processor 42 in sets relating to parallel paths through the body. Each output signal is then modified by combining it with weighted components of other output signals of its own set; the weighting being in accordance with a function which is negative, and decreases in amplitude as the distance from the path giving rise to the output signal being weighted to the path giving rise to the output signal being modified increases. The modified output signals are then additively combined in accordance with the inter relationships of the paths to which they relate, in accordance with a layergramming procedure, the modification of the output signals being such as to compensate for the known inaccuracies of conventional layergrams.

Additional refinements may be made to the apparatus shown in FIG. 1 if desired. For example blocks of X-ray absorbent material could be disposed between the source 25 and the body 3 and/or between the body 3 and the detector array 26 to tend to reduce variations in the degree of absorption suffered by the radiation on traversing paths of different lengths through the body 3. Moreover, the blocks may be arranged to impart a specified attenuation to the radiation when it traverses paths wholly outside the body 3 and its supporting bed so as to permit the sensitivities of the various detectors to be monitored.

In some circumstances, it can be difficult to physically accommodate the thirty detectors in side-by-side relationship in the array 26 and in such cases it is desirable to stagger the detectors in distance from the source the stagger, of course, being kept to a minimum.

In accordance with an example of this invention, as shown in part in FIG. 2, a sensor 43 (for example an e.c.g. pick-up) is used to sense the motion of the patient's heart. This sensor 43 provides electrical signals, of the form shown schematically at 44, which are applied to a movement window selecting circuit 45. Circuit 45 may be merely a threshold circuit which provides an output signal of square waveform whenever the signals 44 exceed the threshold level. It comprises a circuit of known kind which enables upper and lower threshold levels to be set independently of one another and provides an output signal of square waveform whenever the signals 44 have an amplitude which lies within the window region between the two threshold levels. In either event, the output signals from the circuit 45 are applied to a control circuit 46, which also receives output signals from a position co-ordinate generating circuit 47. Circuit 47 comprises means for producing an outline picture of the irradiated region of the patient's body, relative to which a spot 48 of variable size can be moved to indicate the location of the patient's heart in said region. Co-ordinates indicative of the centre of the spot 48 on the outline picture and of the dimensions of the spot, are generated in known manner and applied to the control circuit 47.

In the control circuit 46, the signals from circuits 45 and 47 are correlated to determine the time of commencement of a lateral scanning movement of the source 25 and the detectors 26 relative to the patient's body to ensure that, when the radiation passes through the patient's heart, the heart is in the position, or range of positions, selected by operation of the movement window selecting circuit 45. The control circuit 46 feeds the control circuit 36 (FIG. 1) which is effective to generate the operating signals for the driving motor for disc 13 (FIG. 1) and for the motor 22 (FIG. 1).

Preferably, in this embodiment, the motor 22 drives the roller 21 via an electrically operable clutch, and the arrangement is such that, the yoke 16 having completed one lateral scanning movement, the photocell/detector unit 35 detects an end-of-scan marking on the graticule 34 and produces a signal which causes control circuit 36 to energise the motor driving disc 13 to effect a single rotational step of the member 1 relative to the body, and to reverse the direction of drive of motor 22. This having been done, control circuit 36 disconnects the clutch through which the motor 22 drives the roller 21 and the motor rotates freely until the control circuit 47 produces a signal indicating that the lateral scan can commence. This signal is fed to control circuit 36 whereupon a signal is generated to connect the clutch and then a second lateral scan is effected.

The control circuit 36 is provided with gating circuits of known kind which prevent it responding to signals from the circuit 47 unless an end-of-scan signal has been received from circuit 35, a subsequent rotational step of the member 1 has been executed and the motor 22 has been reversed.

Other techniques can be adopted if desired. For example the lateral and rotational scanning movements could be effected regularly, (i.e. not in synchronism with the heart) and the signals supplied by a sensor such as 43 may be recorded along with the relevant output signals to enable account to be taken at a later stage of movement of the patient's heart. As another alternative, the source of X-rays could be turned off or obturated if the radiation is projected through the region in the vicinity of the heart whilst the movement of the heart is outside the range set by a window selecting circuit such as 45. This would mean of course that, unless the scan were allowed to proceed further than 180°, the data relating to the heart could be sparse, but this would not matter if it was not the heart but another region of the body that was of interest; the object in this case being to reduce blurring effects and/or the production of artifacts, due to motion of the heart, which could deleteriously affect the accuracy of evaluation of the coefficients in the region of interest.

It could be advantageous to obtain signals such as 44 from the sensor 43 over a reasonable period before the examination of the patient commences so that respective lateral and rotational scanning rates can be determined in advance with the object of reducing to a minimum the 'dwell' times when the motor 22 is running but its clutch is disengaged. In any event, it is advantageous to turn off or obturate the X-radiation whilst said clutch is disengaged.

It is, of course, possible to repeat the scanning procedure in respect of several adjacent slices of the patient's body so as to build up information relating to a volume of the body.

What I claim is:

1. Radiographic apparatus comprising a source of penetrating radiation disposed to project radiation through a cross-sectional slice of a patient's body along at least one substantially linear beam path, detector means disposed to receive the radiation emergent from the body along said at least one beam path, and to provide output data indicative of the amount of radiation so detected, lateral scanning means for scanning said source and detector means laterally across said slice, alternate lateral scanning movements being in opposing directions, and rotational scanning means for scanning said source and said detector means angularly around said slice, means for detecting the heartbeats of said patient and means for synchronising said lateral scanning to said heartbeats.

2. Apparatus according to claim 1 wherein said means for synchronising said lateral scanning movements to said heartbeats includes window selector means for selecting a range of movement amplitudes which can be assumed by the heart while it is irradiated, position indicator means for indicating the position of the heart in the slice and control circuit means for receiving signals from said window selector means and said position indicator means to produce lateral scan initiating signals arranged to initiate each lateral scanning movement at such a time that the radiation is transmitted through the heart while the amplitude of its movement is within said range.

3. Apparatus according to claim 1 wherein said source produces a fan-shaped distribution of radiation and said detector means comprises a plurality of individual detectors disposed across said distribution, each arranged to receive radiation projected along a respective beam of said distribution.

4. Apparatus according to claim 1 wherein said rotational scanning means includes a geneva mechanism to rotate said source and said detector means in steps around said slice.

5. Apparatus according to claim 1 wherein said rotational scanning means includes means for holding said source and said detector means at selected angular positions around said slice.

* * * * *